United States Patent [19]
Malthe-Sørensen et al.

[11] Patent Number: 6,153,796
[45] Date of Patent: *Nov. 28, 2000

[54] PROCESS FOR IOHEXOL MANUFACTURE

[75] Inventors: Dick Malthe-Sørensen; Odd Einar Ingvoldstad; Espen Myrbråten, all of Oslo, Norway

[73] Assignee: Nycomed Imaging AS, Oslo, Norway

[*] Notice: This patent is subject to a terminal disclaimer.

[21] Appl. No.: 09/312,956

[22] Filed: May 17, 1999

Related U.S. Application Data

[63] Continuation of application No. 09/120,724, Jul. 23, 1998, Pat. No. 5,948,940, which is a continuation of application No. 08/845,135, Apr. 21, 1997, abandoned.
[60] Provisional application No. 60/028,532, Oct. 21, 1996.

[30] Foreign Application Priority Data

Aug. 29, 1996 [GB] United Kingdom .................... 9618056

[51] Int. Cl.[7] ................................................. C07C 233/05
[52] U.S. Cl. ........................................ 564/153; 424/9.454
[58] Field of Search ......................... 564/153; 424/9.454

[56] References Cited

U.S. PATENT DOCUMENTS

| | | |
|---|---|---|
| 1,548,594 | 7/1925 | Nordal et al. . |
| 4,250,113 | 2/1981 | Nordal et al. . |
| 4,348,377 | 9/1982 | Felder et al. ................................ 424/5 |
| 5,371,278 | 12/1994 | McCarthy et al. . |
| 5,527,926 | 6/1996 | Ranganathan et al. ................. 549/480 |
| 5,948,940 | 9/1999 | Sorensen et al. ....................... 564/153 |

FOREIGN PATENT DOCUMENTS

| | | |
|---|---|---|
| 105 752 | 5/1984 | European Pat. Off. . |
| 108 638 | 5/1984 | European Pat. Off. . |
| 0406992 A2 | 1/1991 | European Pat. Off. . |
| 2726196 | 12/1997 | Germany . |
| 1472050 | 4/1977 | United Kingdom . |
| 1548594 | 7/1979 | United Kingdom . |

OTHER PUBLICATIONS

Oslo Symp. 1982: Ion Exch. Solvent Extr., PAP, V/36–V/43.

*Primary Examiner*—Shailendra Kumar
*Attorney, Agent, or Firm*—Bacon & Thomas

[57] ABSTRACT

The invention provides a process for the production of iohexol comprising reacting 5-acetamido-N,N'-bis(2,3-dihydroxypropyl)-2,4,6-triiodophthalamide with a 2,3-dihydroxypropylating agent, the improvement comprising effecting that said process in the presence of a solvent comprising 2-methoxy-ethanol and, optionally, isopropanol.

5 Claims, No Drawings

PROCESS FOR IOHEXOL MANUFACTURE

This application is a continuation of nonprovisional application Ser. No. 09/120,724, filed Jul. 23, 1998, now U.S. Pat. No. 5,948,940 issued Sep. 7, 1999, which is a continuation of Ser. No. 08/845,135, filed Apr. 21, 1997 now abandoned. Benefit is also claimed under 35 U.S.C. §119(e) of provisional application Ser. No. 60/028,532, filed Oct. 21, 1996.

FIELD OF THE INVENTION

This invention relates to a process for the manufacture of iohexol, 5-[N-(2,3-dihydroxypropyl)-acetamido]-N,N'-bis (2, 3-dihydroxypropyl)-2,4,6-triiodoisophthalamide.

BACKGROUND OF THE INVENTION

Iohexol is a non-ionic iodinated X-ray contrast agent that has achieved considerable market success under the trade name OMNIPAQUE®.

The manufacture of such non-ionic contrast agents involves the production of the chemical drug substance (referred to as primary production) followed by formulation into a drug product (referred to as secondary production). Primary production usually involves a multistep chemical synthesis and a thorough purification stage. Clearly for a commercial drug product it is important for the primary production stage to be efficient and economical.

The final step in iohexol production is an N-alkylation step in which 5-acetamido-N,N'-bis(2,3-dihydroxypropyl)-2,4,6-triiodoisophthalamide (hereinafter "5-Acetamide") is reacted in the liquid phase with an alkylating agent to introduce the 2,3-dihydroxypropyl group at the nitrogen of the 5-acetamido group. Following this reaction, iohexol is isolated from the reaction mixture. This reaction is described for example in SE-7706792-4 where crude iohexol is obtained from the reaction between 5-Acetamide and 1-chloro-2,3-propanediol at ambient temperature in propylene glycol and in the presence of sodium methoxide. After repeated additions and evaporations of the propylene glycol solvent and treatment with anionic and cationic exchange resins, the crude product is evaporated to dryness and crystallized from a second solvent, butanol. The product is then recrystallized twice from butanol.

The N-alkylation step is problematic because of the possibility of by-product formation as a result of O-alkylation, and with N-alkylated iodinated X-ray contrast agents two or more crystallizations are often required in order to remove the O-alkylated by-products. If, as with the iohexol synthesis referred to above, the product is to be crystallized out from a second solvent system, the reaction solvent must first be removed, eg. by evaporation to dryness or by extensive azeotropic distillation. However, as it is known from crystallization theory and experience that even small quantities of residual solvents from previous steps may cause a crystallization process to get out of control due to changes in supersaturation conditions, thorough removal of the reaction solvent is an important step. Solvent removal however is an energy consuming operation which also risks degradation of the product through prolonged exposure to elevated temperatures.

SUMMARY OF THE INVENTION

It has now surprisingly been found that 2-methoxy-ethanol can be used as a solvent for both the 5-Acetamide conversion reaction and for subsequent crystallization of the resulting iohexol thereby avoiding the need for the exhaustive removal of the reaction solvent before purification by crystallization of the crude iohexol product and also reducing the need for multiple crystallizations.

Thus in one aspect the present invention provides a process for the production of iohexol, said process comprising reacting 5-acetamido-N,N'-bis (2,3-dihydroxypropyl)-2, 4,6-triiodophthalamide with a 2,3-dihydroxypropylating agent in the presence of a solvent (the reaction solvent), characterised in that said solvent comprises 2-methoxy-ethanol and, optionally, isopropanol.

Viewed from a further aspect the invention provides a method for the purification of iohexol comprising obtaining a solution of crude iohexol in a first solvent (the crystallization solvent), causing iohexol to separate out from said solvent in solid form and washing the solid iohexol with a further solvent (the washing solvent) whereby to yield iohexol of improved purity, characterised in that said first solvent comprises isopropanol and 2-methoxy-ethanol in a volume ratio of from 93:7 to 85:15 (preferably 91:9 to 87:13 and more preferably 90:10 to 88:12) and in that said further solvent comprises isopropanol.

In a particularly preferred embodiment of the process of the invention, iohexol produced by the process of the invention is subsequently purified by the method of the invention.

DETAILED DESCRIPTION OF THE INVENTION

As set out above, the process and method of the invention involve the use of a reaction solvent, a crystallization solvent and a washing solvent. In all these cases the solvents used may contain further co-solvents beyond the alcohols specified. The presence of such further co-solvents is not preferred and if present they preferably form a minor fraction of the total solvent, eg. less than 10 vol %, preferably less than 5 vol %, more preferably less than 2 vol % and especially preferably less than 1 vol % in total. In the crystallization solvent in particular, if methanol and/or water is present as a co-solvent this is preferably as less than 2 vol %, preferably less than 1 vol % and especially less than 0.5 vol %.

The reaction solvent preferably is 2-methoxy-ethanol; however a mixture of 2-methoxy-ethanol and isopropanol may be used, eg. up to 95 vol % isopropanol may be used, conveniently up to 90 vol % isopropanol, preferably up to 80 vol %, more preferably up to 50 vol % and most preferably less than 10 vol %. The proportion of isopropanol should preferably not be so high that precipitation of iohexol occurs in the reaction mixture at the reaction temperature.

In the crystallization solvent or suspension, the lower limit for 2-methoxy-ethanol content is important to ensure easy dissolution of the crude iohexol. The upper limit is important to ensure iohexol crystallizes out rather than forms an amorphous solid.

The process of the invention is preferably effected in the presence of a base, conveniently an organic or inorganic base which is soluble in the reaction solvent. Inorganic bases, such as alkali metal hydroxides, eg. sodium hydroxide, are preferred. The base may conveniently be used in concentrations of 1.0 to 2.0, preferably 1.0 to 1.5, moles per mole of 5-Acetamide. Where a base is used in the process, the reaction may be terminated by quenching with an acid. Inorganic or organic acids may be used; however inorganic acids, such as HCl, are preferred.

The reaction may be monitored, eg. by HPLC, to determine the appropriate stage at which quenching should take place. Generally, the reaction will be allowed to proceed for several hours, eg. 12 to 48, particularly 18 to 30, before quenching.

The alkylating agent used in the process may be any agent capable of introducing a 2,3-dihydroxypropyl group at the nitrogen of the acetamide group. 1-Halo-2,3-propanediols, eg. 1-chloro-2,3-propanediol, and glycidol are particularly preferred alkylating agents.

The process of the invention is conveniently effected at elevated temperature, eg. 25 to 45° C., preferably 30 to 40° C. and most preferably about 35° C.

Following termination of the reaction, the iohexol reaction product may be separated from the solvent, eg. by cooling, solvent evaporation and/or addition of a solvent such as isopropanol in which iohexol is less soluble. The crude iohexol obtained, optionally after washing, eg. with isopropanol, may then be purified preferably by recrystallization.

In the method of the invention, the crude iohexol starting material, typically less than 97.5% purity (by HPLC area percentage), is first dissolved in the crystallization solvent. In one particularly preferred embodiment, the solution used may simply be the reaction mixture from the process of the invention, optionally after adjustment of its salt content, with the isopropanol/2-methoxy-ethanol content of the solvent if necessary also being adjusted, eg. by addition of isopropanol, to fall within the ratios specified above. If this is done, a single crystallization of the iohexol may be all that is required, resulting in savings in equipment, energy and material.

The crystallization solvent may then be partly removed, eg. at elevated temperature and/or reduced pressure, and the resulting iohexol suspension is filtered and the iohexol is washed with the washing solvent, preferably hot isopropanol, before being dried, preferably at elevated temperature (eg. 50° C.) and reduced pressure.

If desired, one or more further recrystallizations from the crystallization solvent may be effected. However, in practice these have not been found to be necessary with the first crystallization yielding iohexol of a purity which is greater than 98.5%, and in particular greater than 99%, and is suitable for use in secondary production. (For secondary production the iohexol should preferably have a content of less than 1%, especially preferably less than 0.6%, (HPLC area percent) of O-alkylation by-products).

This invention is illustrated further by the following non-limiting Examples.

EXAMPLE 1

2-Methoxy-ethanol (278 ml) and sodium hydroxide (18 g) were added to a jacketed glass reactor and stirred for two hours at 20° C. 5-Acetamido-N,N'-bis(2,3-dihydroxypropyl)-2,4,6-triiodoisophthalamide (283 g) was added to the reactor, and the mixture stirred overnight at 45° C., before it was allowed to cool to 30° C. 1-Chloro-2,3-propanediol (45 g) was added to the solution, the temperature set to 35° C. after 90 minutes, 1-chloro-2,3-propanediol (3 g) added after two hours, and the reaction was allowed to proceed for 24 hours before quenching with concentrated hydrochloric acid (1 ml). The reaction mixture was then analyzed by HPLC (water/acetonitrile, 10 cm column), giving the following results:

| | |
|---|---|
| Iohexol | 97.9% |
| 5-acetamido-N,N'-bis(2,3-dihydroxypropyl)-2,4,6-triiodoisophthalamide | 1.03% |
| O-alkylated substances | 0.56% |
| Other impurities | 0.56% |

EXAMPLE 2

Crude iohexol (75 g) containing 0.16 w/w% water was added to a mixture of 2-methoxy-ethanol (43 ml) and isopropanol (325 ml) in a 1 L jacketed reactor equipped with a mechanical stirrer and a cooler. The suspension was heated under stirring (400 rpm) with the following temperature gradient:

20° C. for 30 minutes
20°–70° C. during 60 minutes
70° C. for 90 minutes
70°–93° C. during 60 minutes After reflux at 93° C. was obtained, the temperature was held constant for 20 hours before cooling to 75° C. during 60 minutes. The white suspension was then filtered through a hot vacuum nutch, and the crystals washed on the filter with hot isopropanol (5×15 ml) before drying under reduced pressure at 50° C. overnight.

HPLC analyses (water/acetonitrile, 25 cm column) were performed before and after crystallization. The results are shown in Table I below.

TABLE I

| | HPLC results (area %) | |
|---|---|---|
| Peaks | Before crystallization | After crystallization |
| Iohexol | 97.3 | 99.1 |
| 5-acetamido-N,N'bis(2,3-dihydroxypropyl)-2,4,6-triiodoisophthalamide | 0.99 | 0.28 |
| O-alkylated substances | 0.68 | 0.51 |
| Other related substances | 0.99 | 0.15 |

What is claimed is:

1. In a process for the production of iohexol comprising reacting 5-acetamido-N,N'-bis (2,3-dihydroxypropyl)-2,4,6-triiodoisophthalmide with a 2,3-dihydroxypropylating agent, the improvement comprising effecting said process in the presence of a solvent comprising 2-methoxy-ethanol and isopropanol.

2. A process as claimed in claim 1, wherein said solvent comprises 2-methoxy-ethanol and up to 95 vol. % isopropanol.

3. A process as claimed in claim 1, wherein said solvent comprises 2-methoxy-ethanol and up to 50 vol. % relative thereto of isopropanol.

4. A process as claimed in claim 1, wherein said solvent comprises 2-methoxy-ethanol and up to 10 vol. % relative thereto of isopropanol.

5. A process as claimed in claim 1, wherein said 2,3-dihydroxypropylating agent is a 1-halo-2,3-propanediol or glycidol.

* * * * *